United States Patent [19]

Beavin

[11] Patent Number: 5,503,149
[45] Date of Patent: *Apr. 2, 1996

[54] COMPUTER SIMULATION OF LIVE ORGAN USING ARTHROSCOPIC AND/OR LAPAROSCOPIC DATA

[76] Inventor: William C. Beavin, 5527 Waterman #2E, St. Louis, Mo. 63112

[*] Notice: The term of this patent shall not extend beyond the expiration date of Pat. No. 5,273,038.

[21] Appl. No.: 175,793

[22] Filed: Dec. 27, 1993

Related U.S. Application Data

[63] Continuation-in-part of Ser. No. 801,914, Dec. 3, 1991, Pat. No. 5,273,038, which is a continuation-in-part of Ser. No. 550,343, Aug. 2, 1990, abandoned.

[51] Int. Cl.$^6$ .................. G06F 159/00; A61B 1/313; A61B 1/317
[52] U.S. Cl. .................. 128/653.1; 128/653.2; 128/696; 128/731; 128/733; 382/128; 600/921
[58] Field of Search .................. 364/413.13, 413.14, 364/413.22; 128/4, 5, 653.1, 653.2, 653.4, 696, 731, 733; 348/70, 71, 72, 73; 600/103, 109, 111, 113, 160; 382/6

[56] References Cited

U.S. PATENT DOCUMENTS 5,045,935  9/1991  Kikuchi .................. 358/98
5,045,936  9/1991  Lobb et al. .................. 358/100
5,261,404  11/1993  Mick et al. .................. 128/653.1

*Primary Examiner*—David M. Huntley
*Assistant Examiner*—Joseph Thomas
*Attorney, Agent, or Firm*—Henry W. Cummings

[57] ABSTRACT

A computer system receives two dimensional image data of a heart or other organ to be simulated in three dimensions. It also receives chemical composition data of the heart or other organ, and chemical composition data other parts of the body. These data are put in the computer memory. Then a "Voxel View™" or three dimensional volume rendering program forms images of the organ to be studied. For example, with the heart it generates images of the atria and ventricle. Diagnostic data obtained from a patient conveniently with electrical measurement signals including an electrocardiagram, electromyogram, electroencephalogram, and other diagnostic measured electrical signals obtained from a patient are fed into the system and are placed in computer memory. Arthroscopic and/or laproscopic data obtained from a lens located inside the body of portions of organs of the body of the patient may be inputted as diagnostic data and processed with a "PowerScene™" program. Alternatively the arthroscopic and/or laproscopic data may be inputted as image data and processed with the "Voxel View™" and/or "PowerScene™" program(s). The display device may be a conventional CRT or a small helmet type CRT located on an operating physician's helmet.

20 Claims, 4 Drawing Sheets

COMPUTER SIMULATION OF LIVE ORGAN USING ARTHROSCOPIC AND/OR LAPAROSCOPIC DATA

REFERENCE TO RELATED APPLICATION

This application is a continuation-in-part of application Ser. No. 801,914 filed Dec. 3, 1991 now U.S. Pat. No. 5,273,038, which in turn is a continuation in part of application Ser. No. 550,343, filed Aug. 2, 1990, now abandoned.

BACKGROUND OF THE INVENTION

U.S. Pat. Nos. 3,453,745 and 3,552,036 disclose electronically operated means to simulate, control, and modify ECG signals. The signals are displayed on standard oscilo-scope-type monitors. However, these patents only address means to simulate ECG signals.

U.S. Pat. No. 4,091,549 discloses means to trace heart electrical activity through specific points of a heart by means of illumination of specific parts of an illustration of a heart.

U.S. Pat. No. 4,254,562 discloses means to trace blood flow through specific points of a heart model or other component of a living organism.

OBJECTS OF THE INVENTION

One object of the invention is to display to an observer a pictorial image of a patient's organ generating EEG, EMG, ECG, or other diagnostic electrical signals as these signals are occurring in the patient's organ. The diagnostic signals are commonly voltages measured of the organ tissue indicating expansion and contraction of the organ.

Another object is to provide a three dimensional interactive view of an organ operation from electrical measurement signal type information.

Another object is to provide the operator with a view of an active, working organ model driven from electrical measurement signal type information in three dimensions.

Another object is to allow the operator to manipulate various characteristics and dynamics of the modelled organ or the signals from an actual or simulated EEG, EMG, ECG, or other diagnostic electrical measurement signal type monitor and observe the results on interactive, three dimensional graphical models for study, teaching, diagnosis, and research purposes.

Another object is to provide the capability to surgically or chemically interact with, probe, or explore the object of study.

Another object is to provide the capability to do the foregoing with the heart or other organs of the patient's body.

Another object is to input arthroscopic and/or laparoscopic data as one or more diagnostic signals into the system.

Another object is to process arthroscopic and/or laparoscopic data with a "PowerScene™" computer program alone or in combination with a physiological model program in the computer system.

Another object is to input arthroscopic and/or laparoscopic data as image data into the computer system.

Another object is to process the arthroscopic and/or laparoscopic data in the computer system with a "Voxel View™" and "PowerScene™" program acting together in the computer system.

SUMMARY OF THE INVENTION

A computer system receives two dimensional image data of a heart or other organ to be simulated in three dimensions. It also receives chemical composition data of the heart or other organ, and chemical composition data of other parts of the body. These data are put in the computer memory. Then a Voxel View or three dimensional volume rendering program forms images of the organ to be studied. For example, with the heart it generates images of the atria and ventricle. Diagnostic data obtained from a patient conveniently with electrical measurement signals including an electro-cardiagram electro-myogram, electro-encephalogram, and other diagnostic measured electrical signals obtained from a patient are fed into the system and are placed in computer memory. Physiological diagnostic data of the patient including the strength, weakness and other parameters of the organ, is also supplied into the system. This can be done manually with a keyboard or mouse, or may be automatically supplied from a hard disk, a floppy disk or a tape. This is also fed into memory and is used to modify the three dimensional image data of the organ. This data is then synchronized with the electrical signal diagnostic data. Conveniently the first derivative of the electrical data signal is taken, and P and Q waves determined from the derivative. From this information the organ, including sub-parts, may be simulated. This data may be fed in black and white or preferably in color to a device (CRT) which shows the organ for visualization, operation simulation, or training. Arthroscopic and/or laparoscopic data obtained from a lens located inside the body of portions of organs of the body of the patient may be inputted as diagnostic data and processed with a physiological model program alone and/or with a "PowerScene™" program in the computer system. Alternatively, the arthroscopic and/or laparoscopic data may be inputted as image data and processed with the "Voxel View™" and/or "PowerScene™" programs in the computer system. The CRT may be a small helmet CRT used on a physician's helmet.

THE DRAWINGS

SUMMARY OF OPERATION

Figure 1:
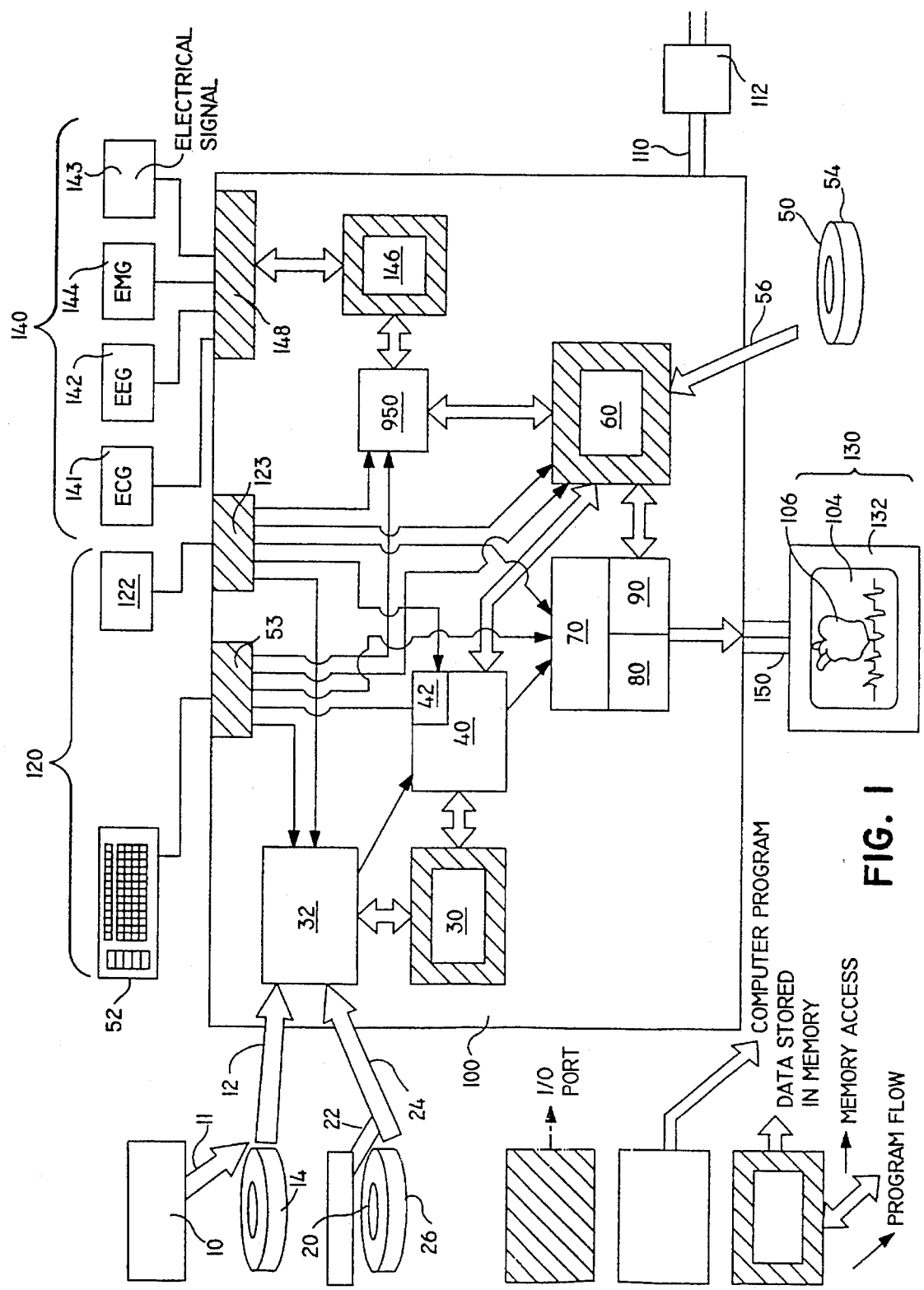
FIG. 1 is a schematic representation of the three dimensional organ monitor of the present invention.

FIG. 1 is a block diagram of the overall system. Five major features are described.

One feature is the interactive devices (120), which may be hand generated data including keyboard (52), mouse (122), touch sensitive screen, light pen, or other device. Data may also be introduced by a voice command signal.

Another feature is to input chemical composition and dimensional image data. This may come from several sources, including Nuclear Magnetic Resonance Imaging Data (11), Computerized Tomography Data (22), or Interactive Device Generated Data, which may come from magnetic tape (14), (26), (50) or data in computer memory or from an appropriate interactive device. Physiological diagnostic data may be provided through line 56.

Another feature is the diagnostic input signals (140). These may be Electrocardiogram (ECG) signals (141), Electroencephalogram (EEG), signals (142), Electromyogram (EMG) signals (144), or other diagnostic data and/or electrical input signals (143).

Another feature is the output device (130), in the preferred version being a cathode ray tube (CRT) (132).

Another feature is the Graphics Image Generator Computer System (100). Within this computer system, which may be composed of several networked computers, several computer programs (32), (40), (70), and (950) run, accessing several blocks of memory (30), (60), and (146). These utilize the described input and output means to graphically display a three dimensional object that reflects input activity and can be manipulated by the user.

Another feature is to input arthroscopic or laparoscopic data that may be inputted as diagnostic data through electrical input (143) and processed with physiological model program (950) and/or with "PowerScene™" program.

Another feature is to input arthroscopic and/or laparoscopic data as image data through image line 12. It may be processed with "Voxel View™" program alone or in combination with "PowerScene™" program in the computer system.

Another feature is that the the CRT displaying the image may be a small CRT mounted upon an operating physician's helmet. Such physician's helmet are well-known in the art. An example of such a physician's helmet is the Kaiser Sim-Eye available from Kaiser Electro-Optics; 2752 Loker Ave, West; Carlsbad Calif. 92008.

DETAILED DESCRIPTION OF PREFERRED EMBODIMENT

In accordance with the present invention, a Nuclear Magnetic resonance Scanner such as G.E. Medical Systems Model No. MR Signa Advantage 1.5 Tesla (NMRS) General Electric Co., Milwaukee, Wis., (10) provides Imaging Data (11) in grey scale two dimensional slice format. It is used as one input to the Graphics Image Generator Computer System (100). This data is ready available and can be gathered from the patient undergoing diagnosis, or from pre-recorded data from some other NMRS source. The data may enter the system via a digital data communication link (12), which enters the Graphics Image Generator Computer System (100) through a provided communications port, or read from a computer memory or magnetic tape (14). This data represents two dimensional slices of the heart or other object for study which are used to generate a three dimensional picture.

A computerized Tomography Scanner (20) such as a Siemens Medical Systems Somatom Plas supplies Scan Data (22) in grey scale two dimensional slice format is also used as input to this system. This data is readily available, and can be gathered from the patient undergoing diagnosis, or from pre-recorded data from some other CTS source. The data may enter the system via a data communications link (24) through a provided communications port, or read from a storage media, such as magnetic tape (26), hard discs and floppy discs. As an example, the chemical composition of selected parts of the body may be inputed. Other sources of chemical composition data may be used as inputs as well.

A three dimensional Volume Rendering program, (32) such as "Voxel View™", which reads, CTS, NMRS, or similar data into memory (30) is activated in the Image Generator Computer System (100) to receive the data from communications links (12) and (22). "Voxel view™" is a Registered Trademark of Vital Images, Inc. A brochure is in the application file, and is available from them at P.O. Box 551, Fairfield, Iowa 52556, (515) 472-7726. The data (30) is then ready to be manipulated by software (40) running in the Image Generator Computer System (100). For example, Silicon Graphics Models Nos. 4D/GTB, GTXB, or VGXB process the input data into a format suitable to the model dynamics methods. The software (40) comprises a conversion program which puts the data into a format in memory where each particular part of the heart is identified, so that model dynamics programs (950) can accurately model each part's reaction to stimulus data. The software conversion program (40) is illustrated in FIG. 2.

Figure 2:
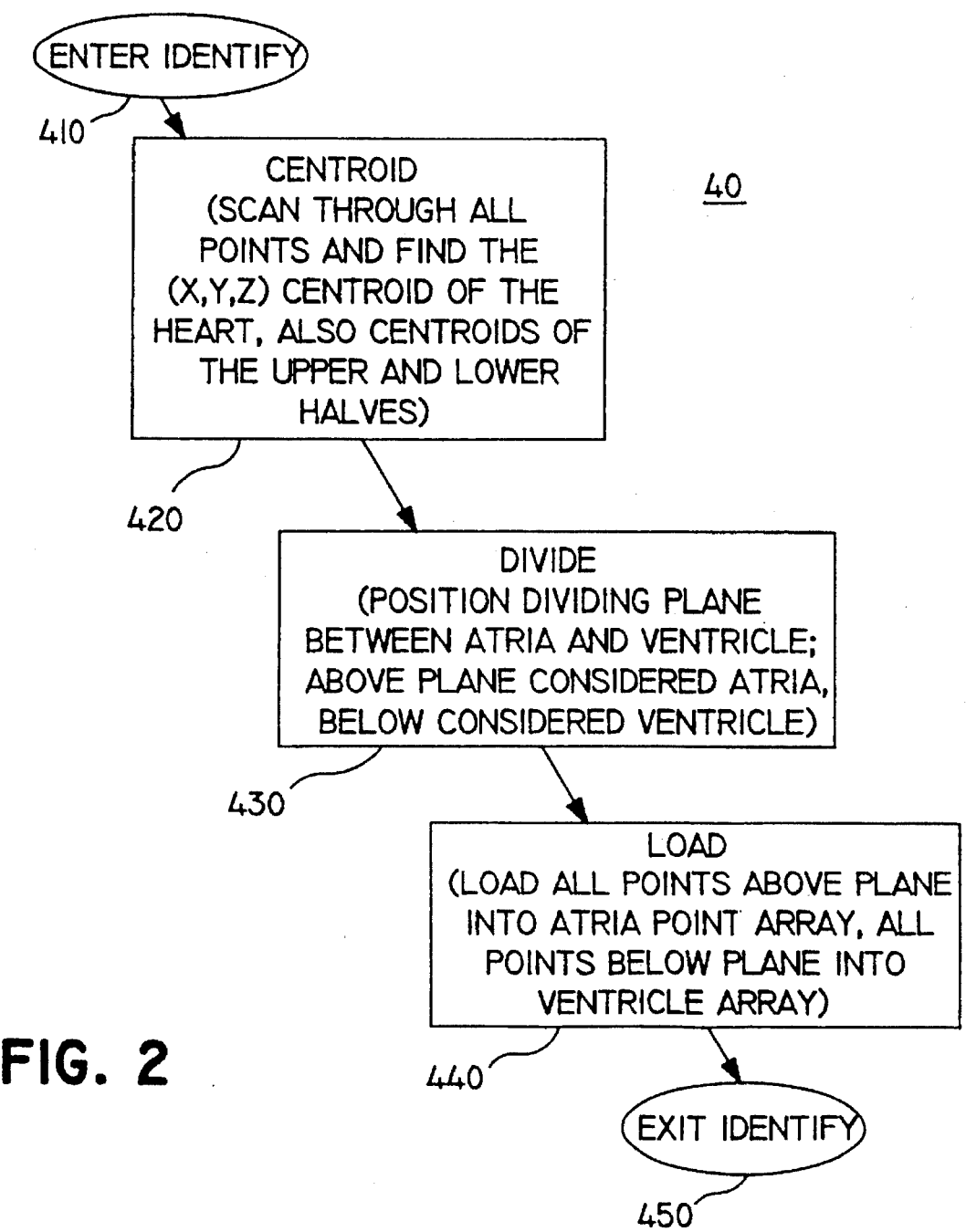
FIG. 2 is a schematic representation of the conversion model program used in the present invention.

FIG. 2 is a block diagram of an example of a simple conversion program (40) that inputs a three dimensional data block (30), and outputs two data point arrays, one for atria, and the other for ventricle points stored in memory (60). The conversion program is entered through entry point IDENTIFY (410).

First, it finds the centroid of all input data points (30) in the CENTROID section (420) of the program. It also determines the centroid of the upper and lower halves of the data. The upper and lower half centroids will be used as reference points for compressing and filling these sections.

The next section, DIVIDE (430) positions a dividing plane passing through the data centroid, dividing it into two halves. This dividing plane could be user defined. Data above the dividing plane is considered the atria and below is considered the ventricle.

The next section, LOAD (440) takes this data and transfers it to two data point arrays, one for the atria, and the other for the ventricle, in a memory section (60). The conversion program then exits (450).

Hand generated data (50) from a keyboard (52) or stored in computer memory or stored on magnetic tape (54), may be fed directly into the system by communication link (56) to add to, modify or correct slice shape data chemical composition data and to input physiological data or that data indicating the relative strength of various parts of the organ to be simulated. Data may be modified for simulation or teaching purposes through Link 56. Modified or simulated data may also be introduced through communications Link 12 and 22.

The data from the conversion program (40) and from hand generation is stored in residual memory (60) in the Graphics Image Generator Computer System (100). The image (104) of the item being studied, in this example a heart (106), is generated from this set of data. This data (60) is also accessed by the model dynamics program (950) where it is modified in the procedure shown in FIG. 3 to reflect activity in the item of study, (here heart 106).

Figure 3:
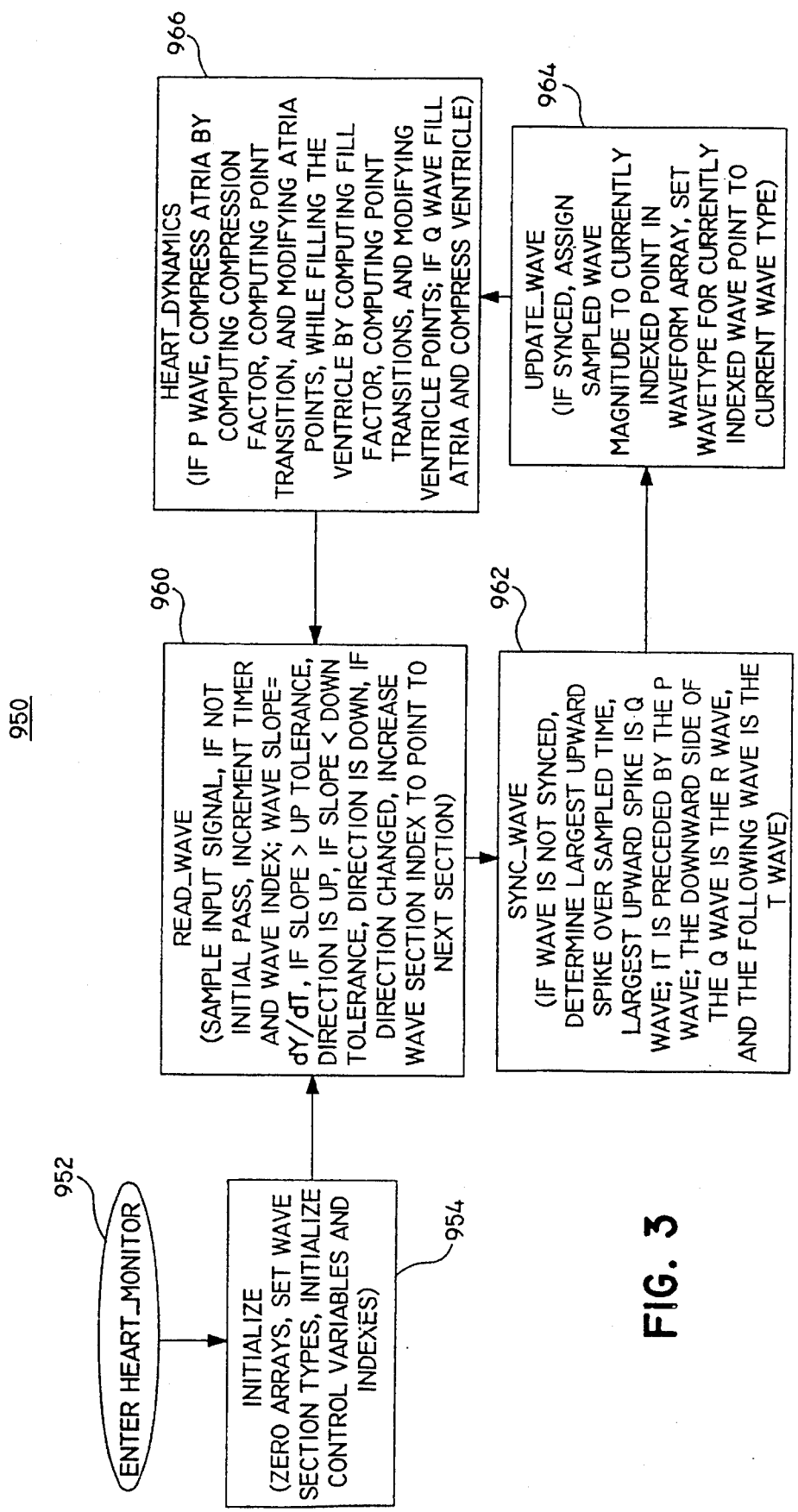
FIG. 3 is a schematic representation of the physiological model dynamics program used in the present invention.

FIG. 3 is a block diagram followed by a computer program of an example of a simple physiological model program for a dynamic heart representation (950). It is composed of an entry point (952), an initialization section (954) where memory blocks are cleared and initialized, and control variables are initialized. This program will access memory blocks (60) set up by the conversion program (40) as shown in FIG. 2.

The physiological model program the enters a loop, beginning with the Read-Wave section (960) where input signals data (146) is accessed. The first derivative of the input signal magnitude with respect to time will indicate whether the signal is increasing or decreasing. With each change of direction, an index identifying the current wave section is incremented. This index identifying the current wave section must be synchronized with the actual input signal, and this synchronization is done in the next section, sync-wave (962).

A flag is set when the wave is known to be synchronized and that section is skipped. Otherwise, the section samples the input signal over a period of time. The largest upward spike is the Q wave, where the wave magnitude corresponds to ventricle compression. When synchronized, the sync flag is set, and this section will not perform again unless synchronization is lost.

The next section is the update-wave section (964). It is performed if the input signal and physiological model program are known to be synchronized (i.e., the sync flag is set). This section accesses the wave section index set in the read-wave section (960). It also accesses the current input signal (148), and assigns this magnitude to the currently indexed point in a memory section known as the wave form array. It also sets the wave type for the currently indexed point in the wave form array to the current wave type using the current wave section index set in the read-wave section (960).

The next section is the Heart-Dynamics Section (966). It accesses the memory (60) where the arrays describing the three dimensional locations of points on the surface of specific contours of the heart are stored. If the currently indexed point has a "P" wave type, the atria is compressed, and the ventricle is filled. A "Q" wave type will fill the atria, and compress the ventricle. Compression of points is done by computing a compression factor, dependent upon the magnitude of the input signal, computing three dimensional point transition using the compression factor, and modifying the array points containing the three dimensional location of the points of the section to be compressed. The same process is done when filling a section, the difference being, a fill factor is used instead of a compression factor. After the heart-dynamics section (966), the physiological model program returns to the read-wave section (960), where the current input signal is again sampled, the direction of signal change is noted, and the loop is repeated.

A Three Dimensional Graphics Program (70), that accesses the data (60) is provided which uses geometric image functions (80) provided by the Graphics Image Generator Computer System (100) to draw an image of the item of study, and reflects the activity of the item, such as a heart, as modelled by the model dynamics program (950). Geometric Image Functions (80), are provided to draw simple shapes or objects. Program (70) uses these functions to produce an image of the item of study such as heart (106). The Three Dimensional Graphics Program (70) is illustrated in FIG. 4.

Figure 4:
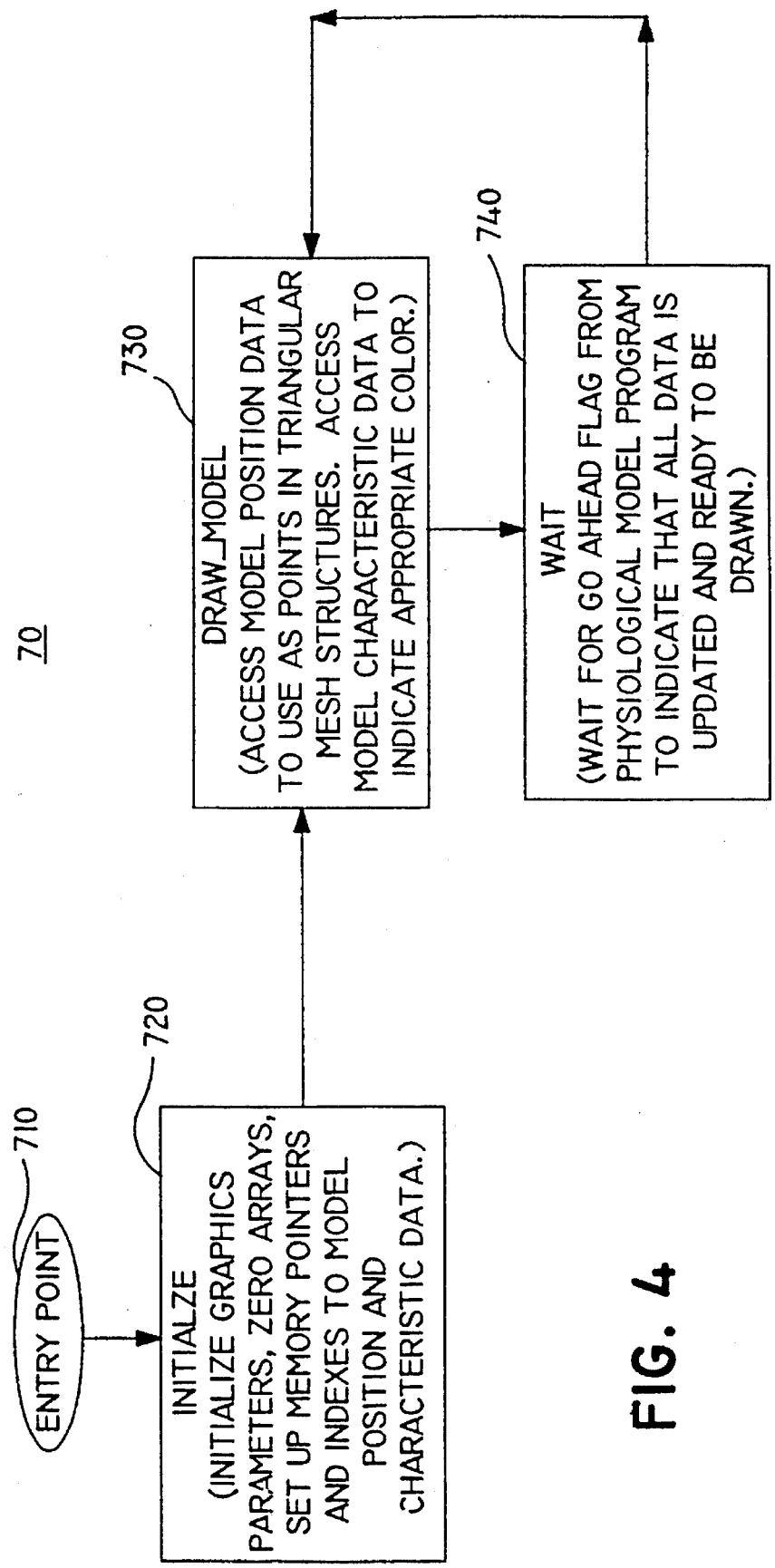
FIG. 4 is a schematic representation of the three dimensional graphics program used in the present invention.

FIG. 4 is a block diagram of the three dimensional graphics program (70). It runs in parallel with the physiological model programs (950) to draw an image of the item of study, in this embodiment a heart.

The program is entered through entry point 3DMODEL (710), and continues into the initialization section (720) where control variables are set up. The program then proceeds to the DRAW_MODEL (730) section, where graphics image functions are accessed to draw the model using simple geometric shapes. In this example, a triangular mesh technique is appropriate, and is fully documented by Silicon Graphics, makers of the preferred embodiment Graphics Image Generator Computer. When the update pass through the graphics image functions is completed, the program waits (740) for the physiological model programs (950) to signal the 3D Graphics Program (70) to update the display. It then repeats the DRAW_MODEL section (730) and continues looping.

The Machine Operating System (90) runs within the Graphics Image Generator Computer (100) and is the interface between the user and the Graphics Generator Machine. The preferred operating system is IRIX, which is well known, and information is available in publications concerning the Graphics Image Generator. For example, see the IRIX System Library, available from Silicon Graphics.

The preferred embodiment Graphics Image Generator is the IRIS 4D/320VGXB from Silicon Graphics of Shoreline Blvd., P.O. Box 7311, Mountain View, Calif. 94037-2011. It has a one million vectors/second and one million polygons/second capacity. Publications are available concerning the use of this system and are found in the IRIS System Library, available from Silicon Graphics. In the preferred embodiment it is equipped with analog input capacity, into which external signals such as ECG (141), EEG (142), EMG (144), or other electrical signals (143) are input.

In the preferred embodiment Graphics Image Generator System, the preferred Graphics Image Generator Computer is the IRIS 4D/320VGXB, and all computer programs are executed within it, but the Graphics Image Generator Computer System may consist of several computers linked or networked together.

Power for the system is 120 volt house current (110) preferably having surge protection (112) included, is also provided.

Interactive Devices (120) such as a keyboard (52) and mouse (122) are supplied with the Graphics Image Generator Computer (100). The preferred devices are a silicon graphics keyboard, model number EO 3410051, part number 30097 and a silicon graphics mouse, model number M4. The keyboard (52) connects to the keyboard port (53), and the mouse (122) connects to the mouse port (123) provided with the Graphics Image Generator Computer (100). These interactive devices (120) interact with all software programs (32), (40), (70), and (950) running in the system.

The image of the item of study is displayed on an output device (130). In the preferred embodiment a Color CRT Terminal (132) such as a Mitsubishi Color Display Model No. HA 3905, AC120v, 60 Hz, 1.6A is used.

Input signals (140) from an electrocardiogram (ECG 141), electroancephalogram (EEG 142), electromyogram (EMG 144) and/or other electrical input signals (143) are supplied to an analog input (148) into computer memory (146) of the Graphics Image Generator (100). These inputs may be direct output from an actual ECG (141), EEG (142), EMG (144), an ECG, EEG, or EMG simulator or other electrical input signals (143). These are well known diagnostic devices, and techniques for generating simulated signals thereof are also well known.

Standard Red-Green-Blue (RGB) connectors (150) are used in the preferred version to connect the CRT terminal (132) to the Graphics Image Generator Computer System (100). These connectors are supplied with the CRT (132) and are conventional.

The Input Data, such as ECG (141), EEG (142), EMG (144), or other electrical input signals (143) is converted in the Graphics Image Generator (100) to digital form at a memory location (146) for use in the model dynamics program (950) by analog input (148).

The Model Dynamics Program (950), such as those for modelling a heart, use either actual or simulated input signals such as ECG (141), EEG (142), EMG (144), or other electrical input signals (143) to determine the reaction of the item of study. It accesses the data (60) for modification to reflect the input signal dynamics, and the updated data is then displayed in the image (104) via the three dimensional graphics program (70) accessing the shared image data in memory (60).

The system described herein consists of input data from various sources including, but not limited to, NMR data (10), CT data (20), hand generated data (50), or other diagnostic data. Also included are appropriate interactive devices (120), such as a keyboard (52), mouse (122), or other devices such as touch sensitive screens, light pens, voice recognition systems, or other compatible interactive means (not shown).

The Graphics Image Generator Computer System (100) is where the software programs run, and input data is stored and manipulated in its memory. The Graphics Image Generator Computer System may consist of several interconnected computers. The software programs, such as Volume Rendering type (32), input conversion (40), three dimensional graphics (70), and physiological model (950), are user activated via appropriate devices, including keyboard (52) or mouse (122). The user first activates the Volume Rendering type input program (32) to bring the NMR (10), CT (20) or other data source into a computer memory block (30). The user then activates the input data conversion program (40), which accesses the Volume Rendering type program output data (30), puts it into a manipulatible form in memory (60) for the physiological model programs (950) and three dimensional graphics program (70) to access.

After the conversion program (40) is completed, the user activates the three dimensional graphics program (70), which accesses the converted data in memory (60), and generates the image (104), in this case a heart (106). The three dimensional graphics program (70) continually loops within itself, accessing the data in memory (60) and updating the display (130) each pass through until the user interrupts the task. While the Three Dimensional Graphics Program (70) is running, the physiological model program (950) is activated to monitor the input signals (140), and modify the data in memory (60) to reflect the input signals.

Meanwhile, the three dimensional graphics program (70) is accessing the memory (60) as updated by the physiological model program (950) and the resultant change is seen in the display (130).

In this case, the programs (70) and (950) are running in parallel in separate processors to take advantage of the dual processors in the preferred embodiment Graphics Image Generator Computer System (100), the IRIS 4D/320VGXB. In accordance with the present invention, the programs could be further parallelized by using more processors, or may run sequentially if only one processor is available. Information on parallelization is available in the Silicon Graphics' Publications Library, available from Silicon Graphics. Other processors may be added by interconnecting the system with other computers to increase processing power, or processors may be replaced as faster ones become available.

The programs and parameters used in these models may be modified or updated depending on the intent of the study or diagnoses, and may model a wide variety of body functions including muscles and nerve signals throughout the body or bodies. Any object with three dimensional data and knowledge of its properties available may be modelled by this system.

Another embodiment of the present invention involves the use of arthroscopic video data or laparoscopic video data which is utilized to example through a fiber optic link and a lens located inside the body, and a camera tophotograph actual physical portions of organs of the body. These devices are well known in the art and the following is an example of where these devices can be purchased, M.P. Video; Kirschner Medical Corp. 63 S. St. Hopkinton Mass. 01748.

This data can be inputted into the present invention through digital data input (143) and then into suitable computer board (148) where the data is processed.

In addition the physiological model program (950) is modified to include a suitable program to control the arthroscopic and laparoscopic data such as "PowerScene™," a program available from Cambridge Research Associates, 1430 Springhill Rd., Suite 200, McClain, Va. 22102. This program is particularly adapted to process arthroscopic and laparoscopic data. This program works in conjunction with the physiological model program (950).

Thus by running the "PowerScene™" program in conjunction with a physiological program (950) the arthroscopic and laparoscopic image is available in the CRT (132) in a manner previously described involving memory (60), through the action of three dimensional graphics program (70), geometric image functions function (80), and machine operating system (90).

Alternatively the arthroscopic or laproscopic data may be inputted at (10) providing image data (11) which is fed into the "PowerScene™" program and works in conjunction with the three-dimensional volume rendering program (32).

The "PowerScene™" program acts in conjunction with the "Voxel View™" program to develop a three-dimensional image which is fed into the memory (30).

Software (40) then transmits this image into the three-dimensional graphics program (70), geometric image function (80), and the operating system (90) will generate the image to be provided in CRT (132).

In addition the CRT (132) may be a very small CRT utilized on an operating physician's helmet so that it can be simultaneously observed by a physician and utilized during surgical operations. Such very small CRT's are known in the art, and an example is Kaiser Sim-Eye from Kaiser Electro-Optics; 2752 Loker Ave, West; Carlsbad, Calif. 92008.

```
        PROGRAM HEART_MONITOR
*
* This is a simple Heart Dynamics program.
*
        COMMON/CONTROL_COMMON/
    .  TIME
    ., DT
    ., INITIAL
        PARAMETER
    .  WAVE POINTS = 200
    ., EKG = 0
```

```
., EMG = 1
., EEG = 2
., P1WAVE = 0
., P2WAVE = 1
., QWAVE = 2
., RWAVE = 3
., SWAVE = 4
., T1WAVE = 5
., T2WAVE = 6
., T3WAVE = 7
., FLAT = 0
., UP = 1
., DOWN = 2
., NUM_WAVE_SECTIONS = 8
COMMON/WAVE_COMMON/
. WAVE_FORM(WAVE_POINTS)
., WAVE_TYPE(WAVE_POINTS)
., WAVE_SECTION(NUM_WAVE_SECTIONS)
., WAVE_POINT
., WAVE_SECTION_INDEX
., WAVE_TIME
., DIRECTION
., OLD_DIRECTION
., SIGNAL
., SLOPE_UP
., SLOPE_DOWN
*
* Initialize Variables On First Pass
*
  INITIAL = .TRUE.
*
* Loop through program reading in data and
* modifying points.
*
    DO
* ...Initialize specific variables...
    IF(INITIAL) CALL INITIALIZE
* ...Read input signal, increment controls,
*    determine wave slope, and update wave
*    section pointer...
    CALL READ_WAVE
* ...Sync waveform sections correctly...
    CALL SYNC_WAVE
* ...Update currently indexed wave point arrays,
*    if waveform is synced...
    CALL UPDATE_WAVE
* ...Compress/fill various heart section arrays,
*    depending on current wave section and
*    magnitude of current wave...
    CALL HEART_DYNAMICS
    INITIAL = .FALSE.
  END DO
  STOP
  END
    SUBROUTINE INITIALIZE
    INCLUDE 'WAVE_COMMON'
    INICLUDE 'CONTROL_COMMON'
    SLOPE_UP = 2
    SLOPE_DOWN = -2
    DT = 0.025
    WAVE_TIME = WAVE_POINTS * DT
    TIME = 0.0
    SIGNAL = EKG
    DIRECTION = FLAT
    OLD_DIRECTION = FLAT
    WAVE_INDEX = 1
    WAVE_POINT = 1
    WAVE_SECTION(1) = T3WAVE
    WAVE_SECTION(2) = P1WAVE
    WAVE_SECTION(3) = P2WAVE
    WAVE_SECTION(4) = QWAVE
    WAVE_SECTION(5) = RWAVE
    WAVE_SECTION(6) = SWAVE
    WAVE_SECTION(7) = T1WAVE
    WAVE_SECTION(8) = T2WAVE
    WAVE_FORM = 0
    WAVE_TYPE = 0
    RETURN
    END
    SUBROUTINE READ_WAVE
```

```
INCLUDE 'WAVE_COMMON'
INCLUDE 'CONTROL_COMMON'
CALL SAMPLE_INPUT(SIGNAL, INPUT_MAGNITUDE)
IF(.NOT. INITIAL) THEN
   TIME = TIME + DT
   WAVE_POINT = WAVE_POINT + 1
   IF(WAVE_POINT .GT. WAVE_POINTS) WAVE_POINT = 1
   DY = INPUT_MAGNITUDE - WAVE_FORM(WAVE_POINT -1)
   SLOPE = DY/DT
   IF(SLOPE .GT. SLOPE_UP)
      THEN
         DIRECTION = UP
      ELSE IF(SLOPE .LT. SLOPE_DOWN) THEN
         DIRECTION = DOWN
      ELSE
         DIRECTION = FLAT
   END IF
END IF
IF(DIRECTION .NE. OLD_DIRECTION) THEN
   WAVE_INDEX = WAVE_INDEX + 1
   IF(WAVE_INDEX .GT. NUM_WAVE_SECTIONS) WAVE_INDEX = 1
END IF
RETURN
END
SUBROUTINE UPDATE_WAVE
INCLUDE 'WAVE_COMMON'
INCLUDE 'CONTROL_COMMON'
IF(SYNCED) THEN
   WAVE_FORM(WAVE_POINT) = INPUT_MAGNITUDE
   WAVE_TYPE(WAVE_POINT) = WAVE_TYPES(WAVE_INDEX)
END IF
RETURN
END
SUBROUTINE HEART_DYNAMICS
INCLUDE 'WAVE_COMMON'
INCLUDE 'CONTROL_COMMON'
SELECT CASE (WAVE_SECTION(WAVE_INDEX))
   CASE P1WAVE
      CALL COMPRESS_ATRIA
      CALL FILL_VENTRICLE
   CASE QWAVE
      CALL COMPRESS_VENTRICLE
      CALL FILL_ATRIA
   CASE DEFAULT
END SELECT
RETURN
END
SUBROUTINE COMPRESS_ATRIA
INCLUDE 'WAVE_COMMON'
INCLUDE 'CONTROL_COMMON'
DO I = 1, NUM_ATRIA_POINTS
   SQUISH_FACTOR = COMPRESSION * ATRIA_RESISTANCE(I)
   POINT_X_CHANGE = SQUISH_FACTOR*
                        (ATRIA_POINT_X(I) - ATRIA_CENTER_X)
   POINT_Y_CHANGE = SQUISH_FACTOR*
                        (ATRIA_POINT_Y(I) - ATRIA_CENTER_Y)
   POINT_Z_CHANGE = SQUISH_FACTOR*
                        (ATRIA_POINT_Z(I) - ATRIA_CENTER_Z)
   ATRIA_POINT_X(I) = ATRIA_POINT_X(I) - POINT_X_CHANGE
   ATRIA_POINT_Y(I) = ATRIA_POINT_Y(I) - POINT_Y_CHANGE
   ATRIA_POINT_Z(I) = ATRIA_POINT_Z(I) - POINT_Z_CHANGE
END DO
RETURN
END
SUBROUTINE COMPRESS_VENTRICLE
INCLUDE 'WAVE_COMMON'
INCLUDE 'CONTROL_COMMON'
DO I = 1, NUM_VENTRICLE_POINTS
   SQUISH_FACTOR = COMPRESSION * VENTRICLE_RESISTANCE(I)
   POINT_X_CHANGE = SQUISH_FACTOR*
                        (VENTRICLE_POINT_X(I) - VENTRICLE_CENTER_X)
   POINT_Y_CHANGE = SQUISH_FACTOR*
                        (VENTRICLE_POINT_Y(I) - VENTRICLE_CENTER_Y)
   POINT_Z_CHANGE = SQUISH_FACTOR*
                        (VENTRICLE_POINT_Z(I) - VENTRICLE_CENTER_Z)
   VENTRICLE_POINT_X(I) = VENTRICLE_POINT_X(I) - POINT_X_CHANGE
   VENTRICLE_POINT_Y(I) = VENTRICLE_POINT_Y(I) - POINT_Y_CHANGE
   VENTRICLE_POINT_Z(I) = VENTRICLE_POINT_Z(I) - POINT_Z_CHANGE
END DO
RETURN
```

```
        END
        SUBROUTINE FILL_VENTRICLE
        INCLUDE 'WAVE_COMMON'
        INCLUDE 'CONTROL_COMMON'
        DO I = 1, NUM_VENTRICLE_POINTS
           GROWTH_FACTOR = EXPANSION * VENTRICLE_RESISTANCE(I)
           POINT_X_CHANGE = GROWTH_FACTOR*
                                    (VENTRICLE_POINT_X(I) - VENTRICLE_CENTER_X)
           POINT_Y_CHANGE = GROWTH FACTOR*
                                    (VENTRICLE_POINT_Y(I) - VENTRICLE_CENTER_Y)
           POINT_Z_CHANGE = GROWTH FACTOR*
                                    (VENTRICLE_POINT_Z(I) - VENTRICLE_CENTER_Z)
           VENTRICLE_POINT_X(I) = VENTRICLE_POINT_X(I) - POINT_X_CHANGE
           VENTRICLE_POINT_Y(I) = VENTRICLE_POINT_Y(I) - POINT_Y_CHANGE
           VENTRICLE_POINT_Z(I) = VENTRICLE_POINT_Z(I) - POINT_Z_CHANGE
        END DO
        RETURN
        END
        SUBROUTINE FILL_ATRIA
        INCLUDE 'WAVE_COMMON'
        INCLUDE 'CONTROL_COMMON'
        DO I = 1, NUM_ATRIA_POINTS
           GROWTH_FACTOR = EXPANSION * ATRIA_RESISTANCE(I)
           POINT_X_CHANGE = GROWTH_FACTOR*
                                    (ATRIA_POINT_X(I) - ATRIA_CENTER_X)
           POINT_Y_CHANGE = GROWTH_FACTOR*
                                    (ATRIA_POINT_Y(I) - ATRIA_CENTER_Y)
           POINT_Z_CHANGE = GROWTH_FACTOR*
                                    (ATRIA_POINT_Z(I) - ATRIA_CENTER_Z)
           ATRIA_POINT_X(I) = ATRIA_POINT_X(I) - POINT_X_CHANGE
           ATRIA_POINT_Y(I) = ATRIA_POINT_Y(I) - POINT_Y_CHANGE
           ATRIA_POINT_Z(I) = ATRIA_POINT_Z(I) - POINT_Z_CHANGE
        END DO
        RETURN
        END
```

What is claimed is:

1. An organ image generating computer system comprising:
   means for obtaining image data necessary selected from arthroscopic and laparoscopic data directly from a patient;
   means for obtaining patient chemical composition data directly from a patient;
   means for detecting electrical diagnostic data from a patient;
   a computer system including means for inputting said imaging data, said chemical composition data and said diagnostic data into a three-dimensional volume rendering program;
   means for processing said inputted data within said computer system to form an organ image and any movement of said organ; and
   means for transmitting said organ image to a display device where said organ image and any movement of said organ is displayed.

2. An organ image generating system according to claim 1 wherein said means for obtaining image data directly from a patient comprises means for obtaining nuclear magnetic resonance data directly from a patient.

3. An organ image generating system according to claim 1 wherein said means for obtaining image data directly from a patient comprises means for obtaining arthroscopic data directly from a patient.

4. An organ image generating system according to claim 1 wherein said means for obtaining image data directly from a patient comprises means for obtaining laparoscopic data directly from a patient.

5. An organ image generating system according to claim 1 wherein said means for detecting electrical diagnostic data includes means for detecting electrocardiogram data.

6. An organ image generating system according to claim 1 wherein said means for detecting electrical diagnostic data includes means for detecting electromyogram data.

7. An organ image generating system according to claim 1 wherein said means for detecting electrical diagnostic data includes means for detecting electroencephalogram data.

8. An organ image generating system according to claim 1 wherein said means for detecting electrical diagnostic data includes means for detecting arthroscopic data.

9. An organ image generating system according to claim 1 wherein said means for detecting electrical diagnostic data includes means for detecting laparoscopic data.

10. An organ image generating system according to claim 1 wherein said display device is a Cathode Ray Tube (CRT).

11. An organ image generating system according to claim 1 wherein said Cathode Ray Tube (CRT) is a small CRT mounted upon a physician's helmet.

12. A method of modelling an animal organ comprising:
    providing an image generator computer system;
    supplying to said computer system image data selected from arthroscopic and laparoscopic image data;
    supplying to said computer system chemical composition data;
    supplying electrical diagnostic data from a patient to said computer system;
    processing said image data and chemical composition data in said computer system with a volume rendering computer program to form a three dimensional image;
    processing said diagnostic data in said computer system with said three dimensional image to form an organ image and any movement of said organ;
    transmitting said organ image to a display device;
    and displaying said organ image and any movement thereof in said display device.

13. A method of modelling an organ according to claim 12 comprising: obtaining nuclear magnetic resonance image data directly from a patient and supplying said nuclear magnetic resonance image data to said computer system.

14. A method of modelling an organ according to claim 12 comprising: obtaining arthroscopic image data directly from a patient and supplying said arthroscopic image data to said computer system.

15. A method of modelling an organ according to claim 12 comprising: obtaining laparoscopic image data directly from a patient and supplying said laparoscopic image data to said computer system.

16. A method of modelling an organ according to claim 12 comprising: detecting electrocardiogram diagnostic data and supplying said electrocardiogram diagnostic data to said computer system.

17. A method of modelling an organ according to claim 12 comprising: detecting electromyogram diagnostic data and supplying said electromyogram diagnostic data to said computer system.

18. A method of modelling an organ according to claim 12 comprising: detecting electroencephalogram diagnostic data and supplying said electroencephalogram diagnostic data to said computer system.

19. A method of modelling an organ according to claim 12 wherein said display device is a Cathode Ray Tube (CRT).

20. A method of modelling an organ according to claim 19 wherein said Cathode Ray Tube (CRT) is a small CRT mounted upon a physician's helmet.

* * * * *